(12) United States Patent
Dana, III

(10) Patent No.: US 7,086,998 B2
(45) Date of Patent: Aug. 8, 2006

(54) MALE EXERCISE DEVICE

(76) Inventor: Alfred Dana, III, 2805 E. Oakland Park Blvd. #222, Fort Lauderdale, FL (US) 33306

( * ) Notice: Subject to any disclaimer, the term of this patent is extended or adjusted under 35 U.S.C. 154(b) by 516 days.

(21) Appl. No.: 10/693,168

(22) Filed: Oct. 23, 2003

(65) Prior Publication Data

US 2005/0101452 A1    May 12, 2005

(51) Int. Cl.
*A63B 21/72* (2006.01)
*A63B 21/06* (2006.01)
*A61F 5/00* (2006.01)

(52) U.S. Cl. ........................... 482/105; 482/93; 600/38

(58) Field of Classification Search ................ 482/121, 482/127–128, 44, 48–50, 93, 105; 600/38–41
See application file for complete search history.

(56) References Cited

U.S. PATENT DOCUMENTS

| 867,340 | A | * | 10/1907 | Barrie | ........................ | 600/39 |
| 3,926,184 | A | * | 12/1975 | Gehl | ........................ | 600/41 |
| 5,060,934 | A | * | 10/1991 | Winston | ...................... | 482/49 |
| 5,526,803 | A | * | 6/1996 | Kelly | ........................ | 128/95.1 |
| 5,702,330 | A | * | 12/1997 | De Monbrun et al. | ...... | 482/105 |
| 5,800,340 | A | * | 9/1998 | Gekhter et al. | ............... | 600/39 |
| 6,080,090 | A | * | 6/2000 | Taylor et al. | ............... | 482/121 |

* cited by examiner

*Primary Examiner*—Michael A. Brown
*Assistant Examiner*—Fenn C. Mathew
(74) *Attorney, Agent, or Firm*—Richard M. Saccocio

(57) ABSTRACT

An exercise device for strengthening and enlargement of the penis includes a substantially helical spring including a first lever arm, a central spring section having one end integral with one end of the lever arm, and a second lever arm integral with a second end of the spring section, each lever arm having one free end including a retainer element. The device also includes a selectable weight attachable to the spring section and a first flexible elongate pad having a width and length proportioned for engagement about the penis. The device also includes a flexible cord, having opposing ends attached to respective opposite ends of the first pad, passing through the retainer means of the first lever arm. The device also includes a flexible elongate pad having a width and a length proportioned for engagement about the penis, and a flexible cord having opposing ends attached from respective opposite ends of the second pad, the cord passing through the retainer elements of the second lever arm.

12 Claims, 3 Drawing Sheets

US 7,086,998 B2

MALE EXERCISE DEVICE

BACKGROUND OF THE INVENTION

A. Area of Invention

The present invention relates to a male exercise device.

B. Prior Art

As is set forth in U.S. Pat. No. 5,702,330 (1997) to De Monbrun et al, entitled Male Exercise Device and Method, a form of exercise, known as Kegel exercise, was developed by a Dr. Arnold Kegel as a way of helping women regain control of urination after child birth. Such exercises are effective in restoring muscle tone in the perinea area and, in particular, the pubococcygeus muscle. However, many of those who practice the Kegel exercises regularly reported an increase in sensation during intercourse as well as an increase in general sensitivity. See Kegel, A., "Sexual Functions of the Pubococcygeus Muscle." *Western Journal of Surgery*, Vol. 60, pp 521–524 (1952).

In recent years, Kegel exercises have been adapted for males with similar results. Therein, the portion of the penis which extends internally into the male pelvic cavity is surrounded by an extensive network of muscles, the most important of which is the pubococcygeus muscle. In most men, these muscles are quite weak, and strengthening of these muscles may be achieved by performing Kegel exercises. This has resulted in reports of male benefits including stronger and more pleasurable orgasms, better ejaculatory control, and increased pelvic sensation during sexual arousal. See, for example, Crooks and Baur, *Our Sexuality*, $4^{th}$ Ed. (1990) The Benjamin/Cummings Publishing Company and Zilbergeld, Male Sexuality, 1978, Little, Brown & Company.

A suggested Kegel exercise program was outlined in Cooks and Bauer above, at Page 160. This program involves the performing of a series of so-called "short Kegels," i.e., holding a contraction of each Kegel, wherein the number of such short Kegels is gradually increased until one can comfortably perform several dozen at a time, twice daily. Thereafter, "long Kegels" are practiced by holding each contraction for a count of three. Eventually, short and long Kegels in each daily exercise routine are combined, and done twice daily. A male may locate the pubococcygeus muscle by squeezing his pelvic muscle during urination to stop the flow of urine several times. The muscles which are squeezed to accomplish this are the ones which are then used to perform the Kegel exercises. If the correct male Kegel exercise is performed while not urinating, the penis will move slightly upward. Kegel exercises done with a penile erection will cause the penis to move up and down.

The prior art, as reflected in De Monbrun above, is directed to a particular exercise device and method of use thereof, intended to further the historic purpose of male Kegel exercises, that is, stronger and more pleasurable orgasms, better ejaculatory control, and increased pelvic sensation. Said art however does not seek to necessarily strengthen or enlarge the penis.

For many who undertake the time and inconvenience of Kegel exercises, the within invention confers additional benefits if an appropriate exercise device is employed upon the penis during the performance of Kegel and related exercises. Further, traditional Kegel exercises, inclusive of that method taught by said prior art to De Monbrun, are generally directed to males suffering from a weakness in the pubococcygeus muscle which consequently reduces or diminishes some aspect of sexual function. In distinction, the present system has been specifically developed for use by the healthy adult male wishing to strengthen and/or enlarge his penis. Therefore, if the prospective male user is not capable of a complete erection, the present system is not applicable.

SUMMARY OF THE INVENTION

An exercise device for strengthening and enlargement of the penis includes a substantially helical spring comprising a first lever arm, a central spring section thereof having one end integral with one end of said lever arm, and a second lever arm integral with a second end of said spring section, each lever arm having one free end including retaining means. The device also includes means for selectably securing a weight to said spring section and a first flexible elongate pad having a width and length proportioned for engagement about said penis. The device further includes a first flexible cord having opposing ends depending from respective opposite ends of said first pad, said cord passing through said retaining means of said first lever arm. The inventive device yet further includes a second flexible elongate pad having a width and a length proportioned for engagement about said penis, and a second flexible cord having opposing ends depending from respective opposite ends of said second pad, said cord passing through said retaining means of said second lever arm.

It is an object of the present invention to provide an improved male exercise device for the strengthening and enlargement of the penis.

It is a further object of the invention to provide a device of the above type useful in a virility enhancement system for use by healthy adult males.

It is a still further object to provide a device having particular utility in an exercise program for the entire group of male abdominal muscles.

It is a still a further object to provide a device having particular utility in maximizing Kegel exercises.

It is a still further object to provide a device having particular utility in an exercise program for the strengthening of muscles of the base of the penis and muscles behind the glans of the penis.

The above and yet other objects and advantages of the present invention will become apparent from the hereinafter set forth Brief Description of the Drawings, Detailed Description of the Invention and claims appended herewith.

DETAILED DESCRIPTION OF THE INVENTION

Figure 1:
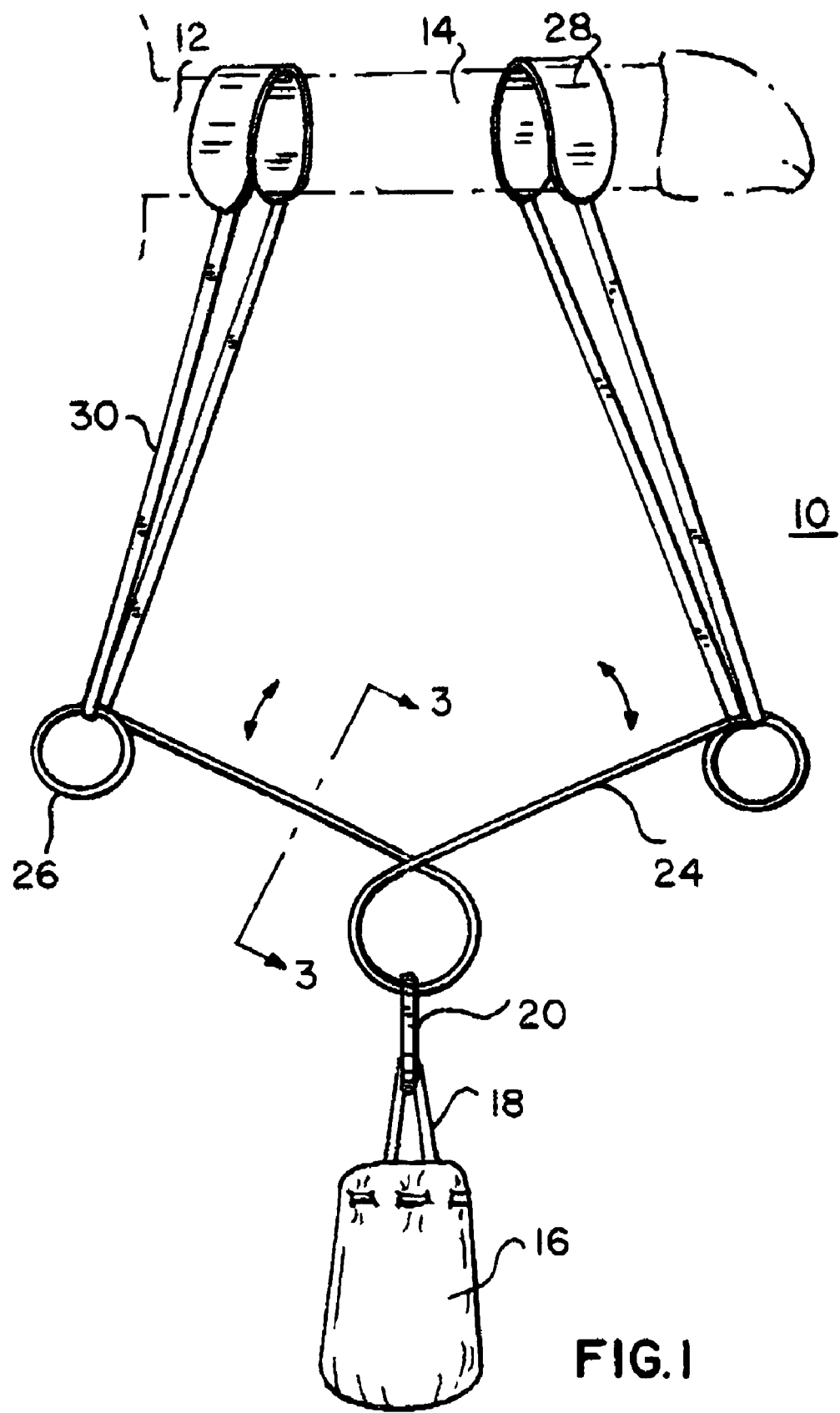
FIG. 1 is a front elevational view of the inventive exercise device attached to an erect penis when unflexed.

With reference to the front elevational view of FIG. 1, an inventive male exercise device 10 may be seen to include first and second flexible elongate pads 28 and 30, each having a width and length proportioned for engagement about an erect penis 14 as is shown in FIG. 1. Therein, a first flexible pad 27 is positioned proximally to base 12 of the penis while a second pad 28 is positioned proximally to glans 15 of the erect penis 14. The positioning of the pads allow the user to adjust the placement on the erect penis to offer even continuity of strength training throughout the entire length and girth of the erect penis and all related pelvic area muscles thereto. It should be noted that the device 10 is intended for use only on an erect penis 14 and offers no benefits on a flaccid penis. An erection is necessary when the device is in place to target the exact muscles to maximize the Kegel exercises.

Ends of said elongate pads 27 and 28 are secured to penis 14 by respective first and second flexible cords 30 and 31. More particularly, opposing ends 32 and 33 of each cord 30/31 depend from opposite elongate ends of the respective pads 27 and 28. At substantially the center of each flexible cord 30 and 31, said cords pass through retaining means 26 and 27 of respective first and second lever arms 24 and 25 of a central spring section 29 of the device. The geometry of central spring section 29 may be more fully seen with reference to the cross-sectional view of FIG. 3.

Figure 2:
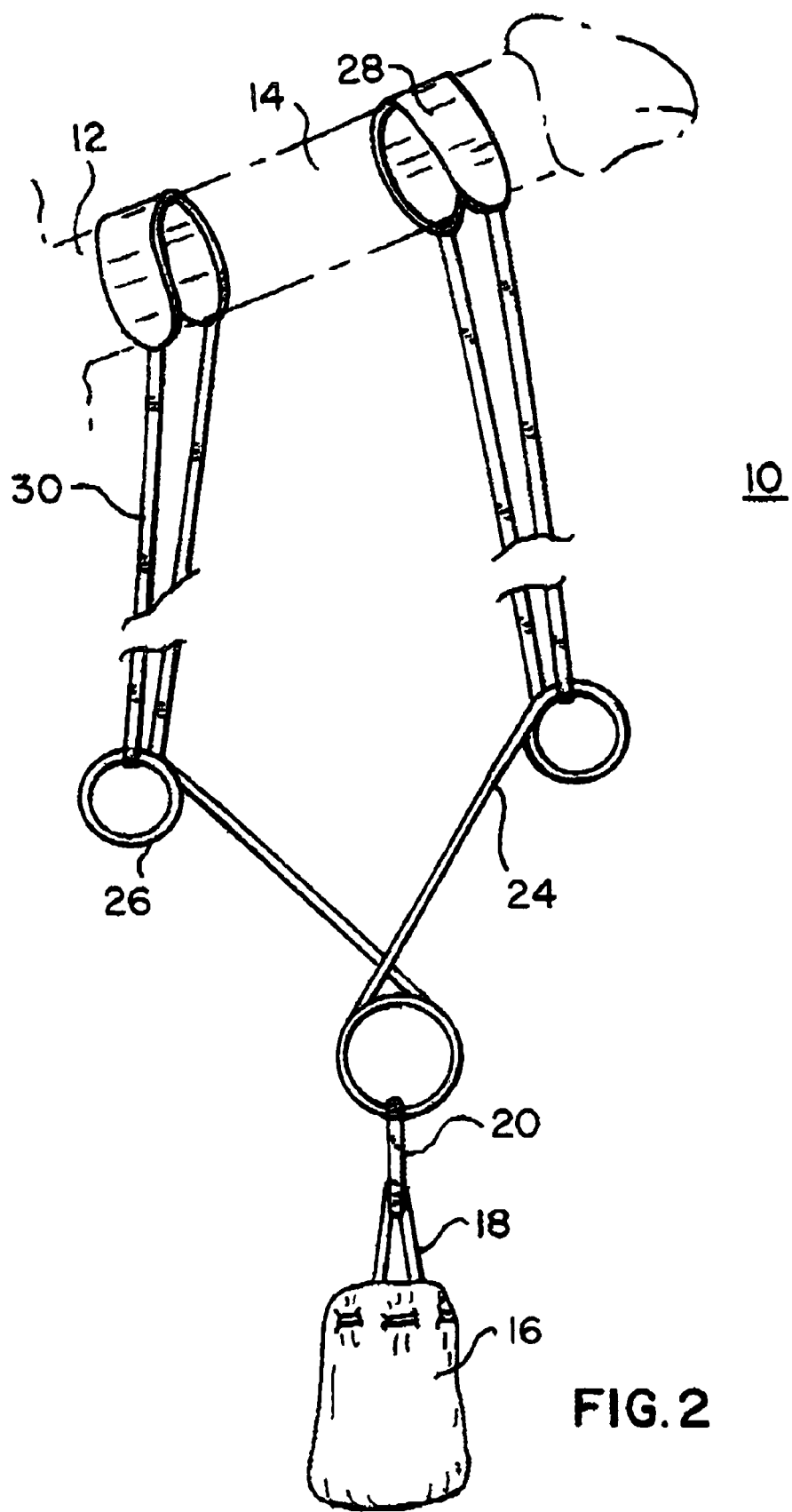
FIG. 2 is a view, similar to that of FIG. 1, however showing the penis in a flexed condition.
Figure 3:
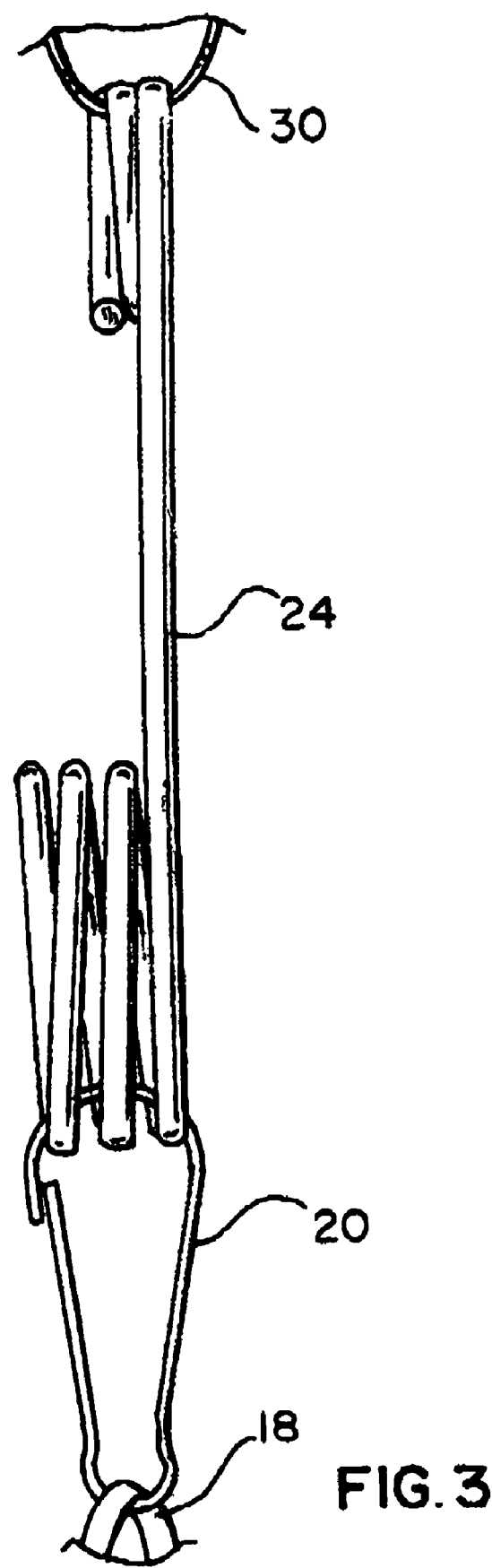
FIG. 3 is a cross-sectional view taken along Line 3—3 of FIG. 1.

Further shown in FIG. 1 is a weighted bag 16 which, through connecting means 18, is connected to a clip 20 which, as is shown in FIG. 3, enables attachment of bag 16 to central spring section 29. It is to be noted that a torsion effect of central spring 29 is such that lever arms 24 and 25 thereof may rotate, or angularly oscillate, along angles A and B in accordance with contractions, flexures or other motions of the erect penis in attempting to overcome the weight contained within bag 16. This may be more fully appreciated with reference to FIG. 2 in which, responsive to a contraction of the pubococcygeus muscle, penis 14 is elevated thereby causing lever arms 24 and 25 to move along angles A and B of FIG. 1 and to thereby decrease the relative acute angle between the lever arms, which maximize Kegel exercises. As may be further appreciated, exercises in the use of the present invention are not limited to the pubococcygeus muscle but, as well, require use of muscles of the lower stomach and other muscles of the pubic area. As such, exercises performed with the inventive device will also result in a tighter and flatter stomach. Further, angular oscillation of angles A and B, also termed the "rocking vibration/bounce effect" of the spring 29, confers various biomechanical advantages, a result of which is to strengthen and enlarge the entire penis as well as enhance latent penis growth.

It is to be appreciated that central spring section 29 and its lever arms 24 and 25 may be formed of various materials including metal wire and plastic. Also, a helical torsion spring, helical extension spring, torsion bar spring, as well as various other types of springs which provide flexural resilience may be suitable to the present application.

It has been found that the length of lever arms 24 and 25 should preferably be in a range of about 5 to about 8 centimeters, and that the length of said flexible pads 27 and 28 should be in a range of about 8 to about 15 centimeters and have a width in a range of about 2 to about 4 centimeters. The total length of flexible cords 30 and 31 is preferably in a range of about 30 to about 50 centimeters. The flexible pads 27/28 and the flexible cords 30/31 may be flexible but may also be composed of a rigid material which is non-flexible. With respect to weights provided within weighted bag 16, selectable weights, preferably in the form of metal balls, marbles or water weights may be placed therein, the same having an aggregate weight in a range of about 15 to about 500 grams.

It is to be further noted that retaining means 26 and 27 of respective lever arms 24 and 25 need not comprise a loop as is shown in FIGS. 1–3 but, in a given embodiment, may comprise any geometry or mechanical means that can secure the center of respective cords 30 and 31 to respective ends of lever arms 24 and 25.

A program using the above-described device would, typically, comprise the following steps:

1. Begin session with a complete erection.
2. In a standing or sitting position, and with feet 60 to 75 cm apart, tighten abdominal muscles, knees slightly bent, shoulders back, thrusting pelvis and penis area outward/forward.
3. Start-out light with one or two balls (about 70 to 140 gm) to warm up, then add weights as needed during your session.
4. Place straps on penis 14, one strap at base of shaft and the other strap approximately 13 mm behind the glans 15.
5. Continue stimulation to glans 15 for a continued erection during lift/flex reps and hold back your ejaculation throughout the session.
6. Begin to lift/flex penis (penis will lift only about 13 to 19 mm upward with each rep) keeping your penis as rigid as possible during each set of six (6) reps.
7. Finish last rep with a 15–30 second hold (use second-hand timer for each hold); rest, then re-establish your erection and repeat the above at least three (3) sets per session daily and continue until you are unable to keep your erection.
8. For best result, perform one complete session of three (3) sets daily, 3 to 4 times a week, at least 10–15 minutes.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

I claim:

1. An exercise device for strengthening and enlarging the penis, the device comprising:
   (a) spring comprising a first lever arm, a second lever arm, and a central spring section therebetween, each lever arm having one free end including retaining means;
   (b) a weight, and means for selectably securing the weight to said central section of said spring;
   (c) a first flexible elongate pad having a width and length proportioned for engagement about said penis;
   (d) a first cord having opposing ends depending from respective opposite ends of said pad, said cord passing through said retaining means of said first lever arm;
   (e) a second flexible elongate pad having a width and length proportioned for engagement about said penis; and
   (f) a second cord having opposing ends depending from respective opposite ends of said second pad, said cord passing through said retaining means of said second lever arm.

2. The device as recited in claim 1, in which said spring comprises a helical torsion spring.

3. The device as recited in claim 1, in which said spring comprises a helical extension spring.

4. The device as recited in claim 3, in which said helical spring comprises a wire spring.

5. The device as recited in claim 3, in which a length of each of said lever arms comprises a range of about 5 to about 8 centimeters.

6. The device as recited in claim 5, in which a length of each of said flexible pads is in a range of about 8 to about 15 centimeters.

7. The device as recited in claim 6, in which a width of each of said pads is in a range of about 2 to about 4 centimeters.

8. The device as recited in claim 6, in which a length of each of said cords comprises a range of about 30 to about 50 centimeters.

9. The device as recited in claim 5, in which each of said retaining means of said lever arms comprises a loop.

10. The device as recited in claim 5, in which said selectable weight comprises a weight in a range of about 15 to about 500 grams.

11. The meeting as recited in claim 3, in which an obtuse angle is defined by an angle formed by an intersection of axes defined by said respective lever arms.

12. The device as recited in claim 1, in which said spring comprises a torsion bar spring.

* * * * *